United States Patent
McIvor et al.

(10) Patent No.: US 11,103,582 B2
(45) Date of Patent: Aug. 31, 2021

(54) METHOD TO ACHIEVE EXTENDED EXPRESSION OF DNA INFUSED INTO LIVER

(71) Applicant: IMMUSOFT CORPORATION, Seattle, WA (US)

(72) Inventors: R. Scott McIvor, St. Louis Park, MN (US); Perry B. Hackett, Shoreview, MN (US); Jason Bell, Maple Grove, MN (US); Myra Christine Urness-Rusten, Plymouth, MN (US); Elena Aronovich, Lauderdale, MN (US); David W. Hunter, Minneapolis, MN (US)

(73) Assignee: IMMUSOFT CORPORATION, Seattle, WA (US)

( * ) Notice: Subject to any disclaimer, the term of this patent is extended or adjusted under 35 U.S.C. 154(b) by 185 days.

(21) Appl. No.: 15/863,740

(22) Filed: Jan. 5, 2018

(65) Prior Publication Data
US 2018/0185487 A1  Jul. 5, 2018

Related U.S. Application Data

(63) Continuation of application No. 14/083,931, filed on Nov. 19, 2013, now abandoned.

(60) Provisional application No. 61/728,036, filed on Nov. 19, 2012.

(51) Int. Cl.
| | |
|---|---|
| *A61K 48/00* | (2006.01) |
| *A61K 47/02* | (2006.01) |
| *A61K 31/353* | (2006.01) |
| *A61K 31/663* | (2006.01) |
| *A61K 33/00* | (2006.01) |
| *A61K 9/00* | (2006.01) |
| *A61K 38/18* | (2006.01) |
| *A61K 38/37* | (2006.01) |
| *A61K 38/48* | (2006.01) |

(52) U.S. Cl.
CPC ............ *A61K 47/02* (2013.01); *A61K 9/0019* (2013.01); *A61K 31/353* (2013.01); *A61K 31/663* (2013.01); *A61K 33/00* (2013.01); *A61K 38/1816* (2013.01); *A61K 38/37* (2013.01); *A61K 38/4846* (2013.01); *A61K 48/0008* (2013.01); *A61K 48/0075* (2013.01); *A61K 48/0083* (2013.01)

(58) Field of Classification Search
None
See application file for complete search history.

(56) References Cited

U.S. PATENT DOCUMENTS

| | | |
|---|---|---|
| 5,227,165 A | 7/1993 | Domb et al. |
| 5,610,053 A | 3/1997 | Chung et al. |
| 5,731,178 A | 3/1998 | Sippel et al. |
| 6,022,564 A | 2/2000 | Takechi et al. |
| 6,090,925 A | 7/2000 | Woiszwillo et al. |
| 6,100,448 A | 8/2000 | Thompson et al. |
| 6,224,794 B1 | 5/2001 | Amsden et al. |
| 6,395,549 B1 | 5/2002 | Tuan et al. |
| 6,613,752 B2 | 9/2003 | Kay et al. |
| 7,534,424 B2 * | 5/2009 | Barsoum ............ A61K 48/0008 424/93.1 |
| 2004/0203158 A1 | 10/2004 | Hackett et al. |
| 2005/0003542 A1 | 1/2005 | Kay et al. |

OTHER PUBLICATIONS

Ranki et al,, IntJ Cancer. Jul. 1, 2007 ;121 (1 ):165-74.*
Burke et al., J Leukoc Biol. Sep. 2002;72(3):417-28.*
Wolff et al, J Virol. Jan. 1997;71 (1 ):624-9.*
Bradshaw et al., Proc Natl Acad Sci USA. Aug. 2, 2005;102(31 ):11029-34. Epub Jul. 25, 2005.*
Dehmlow, et al. "Inhibition of Kupffer cell functions as an explanation for the hepatoprotective properties of silibinin." Hepatology. Apr. 1996;23(4):749-54. doi: 10.1053/jhep.1996.v23.pm0008666328.
Devalapally, et al. "Poly(ethylene oxide)-modified poly(beta-amino ester) nanoparticles as a pH-sensitive system for tumor-targeted delivery of hydrophobic drugs: part 3. Therapeutic efficacy and safety studies in ovarian cancer xenograft model." Cancer Chemother Pharmacol. Mar. 2007;59(4):477-84. doi: 10.1007/s00280-006-0287-5.
Han, et al. "Receptor-mediated gene transfer to cells of hepatic origin by galactosylated albumin-polylysine complexes." Biol Pharm Bull. Aug. 1999;22(8):836-40. doi: 10.1248/bpb.22.836.
Kawakami, et al. "Tol2: a versatile gene transfer vector in vertebrates." Genome Biol. 2007;8 Suppl 1(Suppl 1):S7. doi: 10.1186/gb-2007-8-s1-s7.
Kiwaki, et al. "Correction of ornithine transcarbamylase deficiency in adult spf(ash) mice and in OTC-deficient human hepatocytes with recombinant adenoviruses bearing the CAG promotor." Hum Gene Ther. May 1, 1996;7(7):821-30. doi: 10.1089/hum.1996.7.7-821.
Langer, et al. "Optimization of the preparation process for human serum albumin (HSA) nanoparticles." Int J Pharm. May 12, 2003;257(1-2):169-80. doi: 10.1016/s0378-5173(03)00134-0.
Lutolf, et al. "Synthesis and physicochemical characterization of end-linked poly(ethylene glycol)-co-peptide hydrogels formed by Michael-type addition." Biomacromolecules. May-Jun. 2003;4(3):713-22. doi: 10.1021/bm025744e.
Miskey, et al. "The ancient mariner sails again: transposition of the human Hsmar1 element by a reconstructed transposase and activities of the SETMAR protein on transposon ends." Mol Cell Biol. Jun. 2007;27(12):4589-600. doi: 10.1128/MCB.02027-06.
Miskey, et al. "The Frog Prince: a reconstructed transposon from Rana pipiens with high transpositional activity in vertebrate cells." Nucleic Acids Res. Dec. 1, 2003;31(23):6873-81. doi: 10.1093/nar/gkg910.

(Continued)

*Primary Examiner* — Michael Szperka
(74) *Attorney, Agent, or Firm* — Cooley LLP

(57) ABSTRACT

Materials and methods for treating a patient to express a therapeutic agent comprising administering a Kupffer cell-suppressing substance in combination with a vehicle for introducing, into the patient, an exogenous nucleic acid comprising a sequence for expression of the agent.

14 Claims, 7 Drawing Sheets

(56) References Cited

OTHER PUBLICATIONS

Nichols, et al. "Protein replacement therapy and gene transfer in canine models of hemophilia A, hemophilia B, von willebrand disease, and factor VII deficiency." ILAR J. 2009;50(2):144-67. doi: 10.1093/ilar.50.2.144.

Pavlopoulos, et al. "The DNA transposon Minos as a tool for transgenesis and functional genomic analysis in vertebrates and invertebrates." Genome Biol. 2007;8 Suppl 1(Suppl 1):S2. doi: 10.1186/gb-2007-8-s1-s2.

Tobio, et al. "Stealth PLA-PEG nanoparticles as protein carriers for nasal administration." Pharm Res. Feb. 1998;15(2):270-5. doi: 10.1023/a:1011922819926.

Xu, et al. "CMV-b-Actin Promoter Directs Higher Expression from an Adeno-Associated Viral Vector in the Liver than the Cytomegalovirus or Elongation Factor 1a Promoter and Results in Therapeutic Levels of Human Factor X in Mice." Human Gene Therapy. 2001; 12:563-573.

\* cited by examiner

METHOD TO ACHIEVE EXTENDED EXPRESSION OF DNA INFUSED INTO LIVER

CROSS REFERENCE TO RELATED APPLICATIONS

This patent application is a continuation of U.S. application Ser. No. 14/083,931, filed Nov 19, 2013, which application claims priority to provisional patent application U.S. application No. 61/728,036 filed Nov. 19, 2012, are hereby incorporated by reference herein.

STATEMENT OF GOVERNMENT INTEREST

This invention was made with government support under grant number R44HL072539 awarded by the National Heart Blood and Lung Institute. The government has certain rights in the invention.

TECHNICAL FIELD

The Technical Field relates to treating humans and animals to express a DNA.

BACKGROUND

Stable expression of exogenous DNA in higher animals is desirable for gene therapy. Long-term expression has been achieved in lower animals such as mice. While many processes are known for transfecting cells in animals with exogenous DNA, these processes have resulted in short-term expression in higher animals.

SUMMARY

Materials and methods for achieving long-term expression of an expressible gene have been discovered. These are described herein. These materials and methods are applicable to expression of exogenous DNA in general and are not limited to a particular method of introducing the DNA into the cell. The term exogenous refers to DNA that is introduced into the patient, regardless of whether it is the same as, or different from, the DNA sequences native to, or already in, the host.

An embodiment of the invention is a method of treating a patient to express a therapeutic agent comprising administering a Kupffer cell-suppressing substance in combination with a vehicle for introducing, into the patient, an exogenous nucleic acid comprising a sequence for expression of the agent. Certain embodiments include the case wherein the Kupffer cell-suppressing substance, upon dissolution in aqueous solution, comprises a free gadolinium(III) ion, wherein the Kupffer cell-suppressing substance is free of chelating agents that form three or more coordinate bonds with the gadolinium atom, wherein the Kupffer cell-suppressing substance is free of all chelating agents, wherein the Kupffer cell-suppressing substance comprises a gadolinium (III) salt, and wherein the salt comprises a halide, the salt comprises $Gd(Cl)3$. Certain embodiments include the case wherein the Kupffer cell-suppressing substance is chosen from the group consisting of silibinin, dichloromethylene diphosphonate, gadolinium trichloride, and clodronate. Certain embodiments provide that the therapeutic agent is chosen from the group consisting of a protein, a blood factor, erythropoietin, clotting Factor VIII, clotting Factor IX, an antibody, an antibody fragment, a scFv, and an antigen. The vehicle may be, for instance, a vector, e.g., a vector chosen from the group consisting of an adenovirus, a lentivirus, a retrovirus, an adeno-associated virus, an integrating phage vector, a non-viral vector, a transposon and/or transposase, an integrase substrate, and a plasmid. The Kupffer cell-suppressing substance may be administered before, during, or after administration of the expressible gene. Methods of introducing the DNA, the substance, or both may be, e.g., chosen from the group consisting of intravenous, intramuscular, subcutaneous, and percutaneous injection, and hydrodynamically to the liver.

An embodiment of the invention is a method of treating a patient for expression of a gene comprising administering a nucleic acid that expresses the gene in combination with a Kupffer cell-suppressing substance that comprises a gadolinium atom that is free of chelating agents that form three or more coordinate bonds with the gadolinium atom.

An embodiment of the invention is a system for treating an animal or a human patient to express an exogenous nucleic acid, the system comprising a substance to inhibit Kupffer cells in a pharmaceutically acceptable formulation, a vehicle to administer the exogenous nucleic acid, and a medical device for administration of the exogenous nucleic acid. An embodiment is the system wherein the medical device is adapted to hydrodynamically deliver the vector directly to the liver of the patient. The medical device may comprise a catheter with a size and flexibility for placement in an inferior vena cava of a human (infant, child, adult) and at least one inflatable member for isolating a port of the device within a blood vessel, said port being fluidly connected to a lumen of the catheter.

DETAILED DESCRIPTION

Surprisingly, it has been discovered that long-term expression of exogenous DNA can be achieved by suppression of Kupffer cells in combination with introducing a vehicle for delivering the exogenous DNA into the liver. A series of experiments are described that shed light on how this discovery was made and show that the long-term expression of exogenous DNA is achieved. The method is not limited to any particular method of introducing the DNA. Any suitable vehicle and vector may be used. The method is generally applicable and is not limited to introducing a particular DNA. The method was performed with a large animal model that is accepted as being predictive for humans. Nichols et al., 2009. Protein replacement therapy and gene transfer in canine models of hemophilia A, hemophilia B, von Willebrand disease, and factor VII deficiency. *Ilar Journal* 50:144-67. Small animal models, such as mice, rats, and the like, are not predictive in terms of assessing long term expression in large animals and humans.

Experimental Data, Results, and Discussion

Short Term Expression of Canine Erythropoietin as a Reporter.

Figure 2:
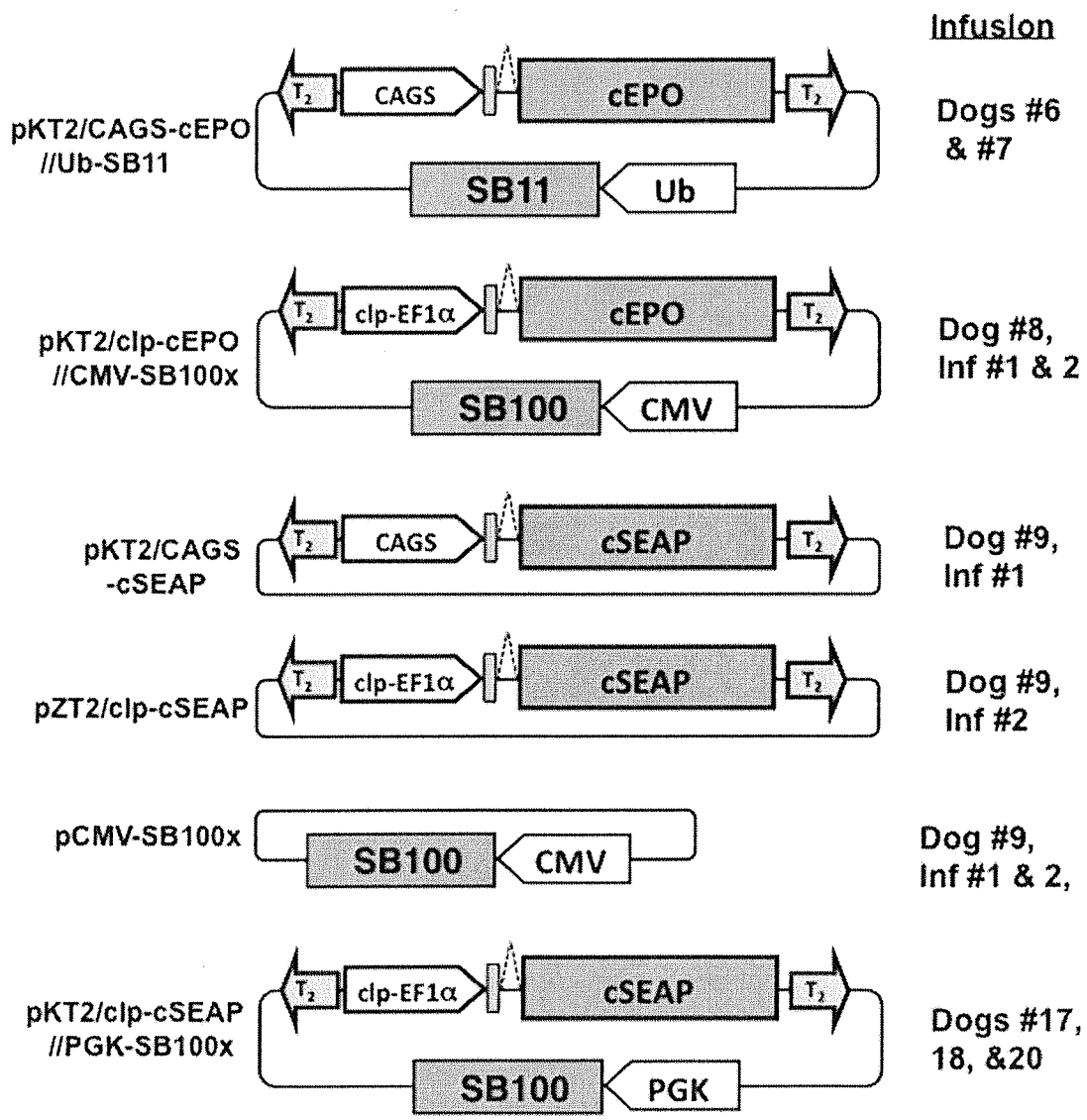
FIG. 2. Transposon and transposase-encoding plasmids. Plasmid names are indicated on the left and experiments in which plasmids were infused are indicated on the right. Transposons contain T2 inverted terminal repeats (shaded arrows) and a reporter gene sequence (shaded boxes) encoding either canine EPO (cEPO), or canine secreted alkaline phosphatase (cSEAP). Reporter gene expression was regulated either by the CAGS promoter or by a CpG-less promoter (clp-EF1a). Promoters are indicated by unshaded block arrows. pKT2/CAGS-cEPO//Ub-SB11 and pKT2/clp-cEPO//CMV-SB100x also contain a ubiquitin-regulated SB11 gene or a CMV-regulated SB100x gene, respectively, exterior to the cEPO-encoding transposon. pKT2/clp-cSEAP//PGK-SB100x contains a PGK-regulated SB100x sequence exterior to the cSEAP-encoding transposon. For the other transposons, SB transposase was provided in trans by co-infusion of a CMV-regulated SB100x expression plasmid (pCMV-SB100x).
Figure 3:
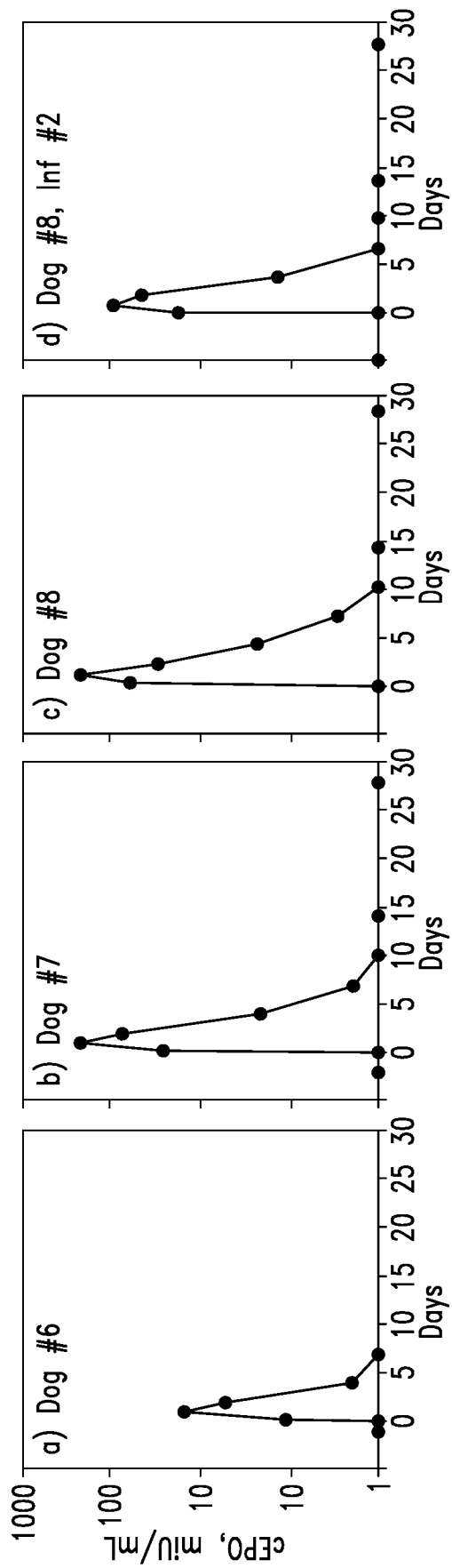
FIG. 3. Canine EPO expression after hydrodynamic DNA infusion in dogs. Dogs were infused as described in the text, with regular collection of blood samples before, during and after the procedure. Plasma samples were assayed for canine erythropoietin (cEPO) by ELISA as described in Materials and Methods. Panel (a) Dog #6 was infused with pKT2/CAGS-cEPO//UbSB11 using the 3-catheter strategy (FIG. 1a). Panel (b) Dog #7 was infused with pKT2/CAGS-cEPO//UbSB11 using the double-balloon strategy (FIG. 1b). Dog #8 was infused twice with pKT2/Clp-cEPO//CS100x using the double-balloon strategy, first at a dose of 10 mg/kg Panel (c) and then at a dose of 2 mg/kg (d).
Figure 4:
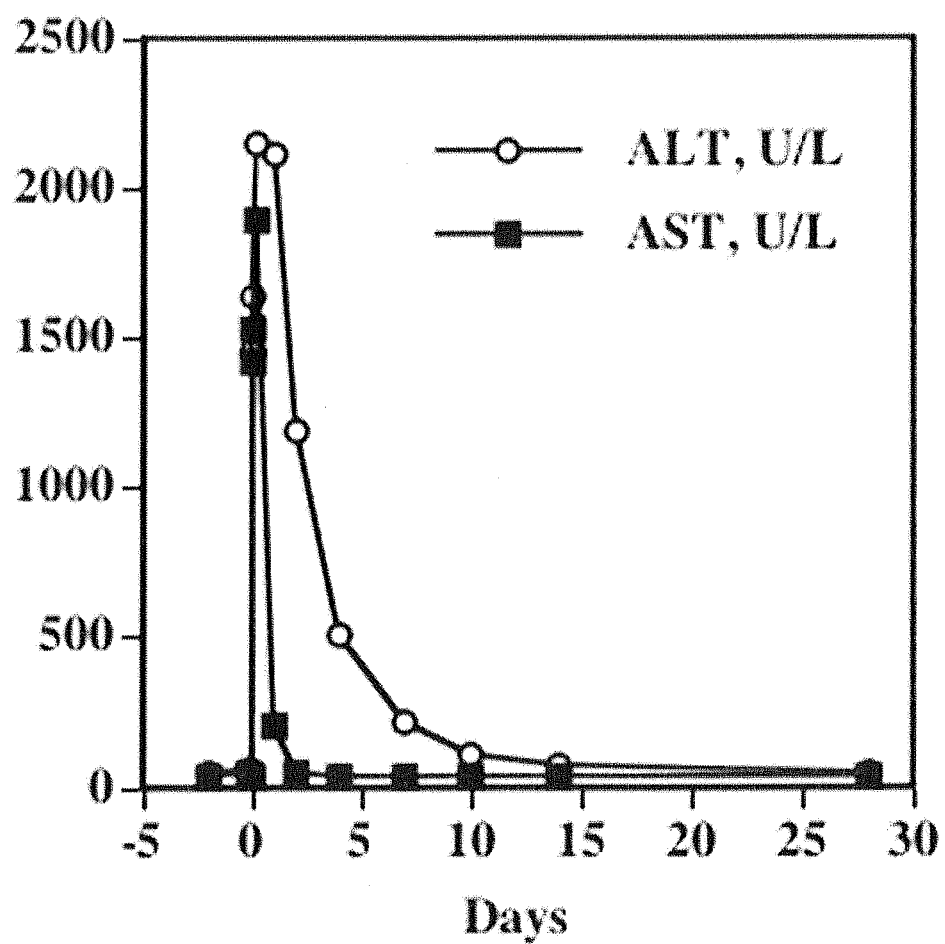
FIG. 4. Serum transaminase levels after hydrodynamic infusion. Serum samples collected before, during and after hydrodynamic infusion were assayed for alanine aminotransferase (ALT) and aspartate aminotransferase (AST). A time course for both enzymes is shown for Dog #7, with AST returning to baseline in two days and ALT returning to near baseline in ten days. Similar time courses were observed for all other infusions, with variation in the peak level of enzyme detected (See Table 1 for peak ALT levels for all infusions).

A three-catheter strategy (FIG. 1a) was used to infuse a canine erythropoietin (cEPO)-encoding expression cassette (pKT2/CAGS-cEPO//Ub-SB11; FIG. 2) at a rate of 12 ml/sec over 17 s. The infusion was well tolerated and cEPO was detectable in the peripheral blood out to four days post-infusion at a peak level of 150 miU/ml 1 day post-infusion (FIG. 3a). There was a transient increase in circulating liver enzymes that normalized after two days (AST) or one week (ALT). There was also a transient drop in hematocrit and white blood cell count around the time of the infusion, but no significant increase in hematocrit subsequent to the infusion (data not shown). This experiment indicated that the delivery procedure was well tolerated but did not result in a level of transgene expression that would be sufficient for a therapeutic effect or for long-term monitoring.

Figure 5:
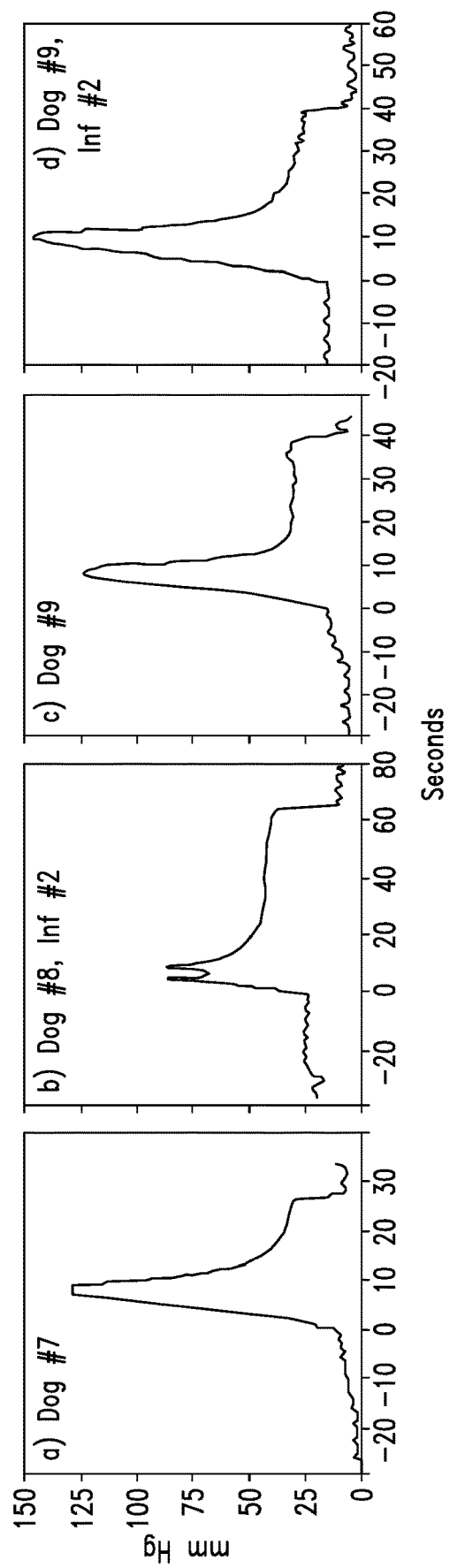
FIG. 5. Intravascular pressures during hydrodynamic delivery in dogs. Intravascular pressure of the occluded region (IVC or left hepatic vein) was assessed before, during and after hydrodynamic infusion. A slight increase in pressure was observed upon inflation of the balloons. For each experiment, the beginning of the infusion is set at time 0. Each of the infusions shown were 10 seconds in duration, during which time there was a substantial increase in pressure that rapidly subsided after the infusion was complete, returning to normal after deflation of the balloons. The entire process from inflation of the balloons, hydrodynamic infusion, through deflation of the balloons required about 60 seconds' elapsed time.

A custom-designed double-balloon catheter was used for occlusion of the inferior vena cava (IVC) and infusion of DNA solution from the same catheter between the two balloons (FIG. 1b). This double-balloon catheter system provided effective occlusion as shown by fluoroscopy (FIG. 1d). In Dog #7, which weighed 5.6 kg, 200 ml of DNA solution containing 60 mg of pKT2/CAGS-cEPO//Ub-SB11 (FIG. 2) was infused at a rate of 20 ml/sec. A computed tomography (CT) scan of the liver conducted one hour after the infusion was normal. IVC intravascular pressure was slightly elevated upon inflation of the balloons, increased dramatically upon initiation of the DNA infusion (maximizing at about 135 mm Hg; FIG. 5a), decreased after the infusion and dropped to normal upon deflation of the balloons. Canine EPO expression peaked at more than 2000 mIU/ml one day post-infusion, but subsequently decayed to background over the next nine days (FIG. 3b). There was a transient increase in liver enzymes in the circulation that normalized within two days (AST) or 14 days (ALT; Table 1). These results indicated that infusion using the double-balloon catheter provided effective delivery of transposon DNA, supporting transgene expression at a potentially therapeutic level without any observable clinical complications or adverse effects. However, expression of the cEPO transgene was still transient, and transgene expression was undetectable one week after infusion of the DNA.

Two more infusions were conducted to test the effectiveness of the DNA infusion technique and to test for high level, long-term transgene expression that could be applied for gene therapy purposes. Experiments for Dog #8 used transposon plasmid pT2/clp-cEPO//CMV-100x (FIG. 2) in which the promoter and enhancer sequences lack CpG sites that could be targets for methylation and subsequent down-regulation. As in Dog #7, 60 mg of DNA (10 mg/kg) was delivered at 20 mL per second (200 ml, 10 seconds) using the double balloon catheter shown in FIG. 1b, which resulted in a peak level of 2100 miU/mL canine EPO 1 day post-infusion that subsequently became extinguished by day 14 (FIG. 3c). Six weeks later a second infusion was carried out into Dog #8, which had grown by this time from 6 kg to 9.8 kg. A lower dose (18 mg, 2 mg/kg) of DNA (pT2/clp-cEPO//CMV-100x) was used, and 1 mg/kg dexamethasone was administered for five days, starting one day prior to delivery of the DNA solution, as an anti-inflammatory measure. Because of the larger size of the animal, a lower peak level of intra-IVC pressure (about 85 mm Hg; FIG. 5b) was achieved during the infusion of 200 ml DNA solution at 20 ml/sec. Nonetheless, a peak cEPO expression level of 1000 miU/ml plasma was observed one day post-infusion, which again became extinguished by day 10 (FIG. 3d).

These results indicated that the double-balloon catheter provided a simplified and low-trauma surgical intervention for infusion of the DNA since it required only a femoral vein cutdown. However, expression of the cEPO transgene was transient in all animals, even with the use of two different transcriptional regulatory sequences. This suggested that physiological responses to elevated cEPO rather than promoter down-regulation might be the cause of the rapid decline in transgene product. Reducing the DNA dose by nearly 80% resulted in only a 50% decrease in cEPO gene expression, indicating that the dose of plasmids was close to saturating.

Limited Term Expression of Canine Secreted Alkaline Phosphatase.

Figure 6:
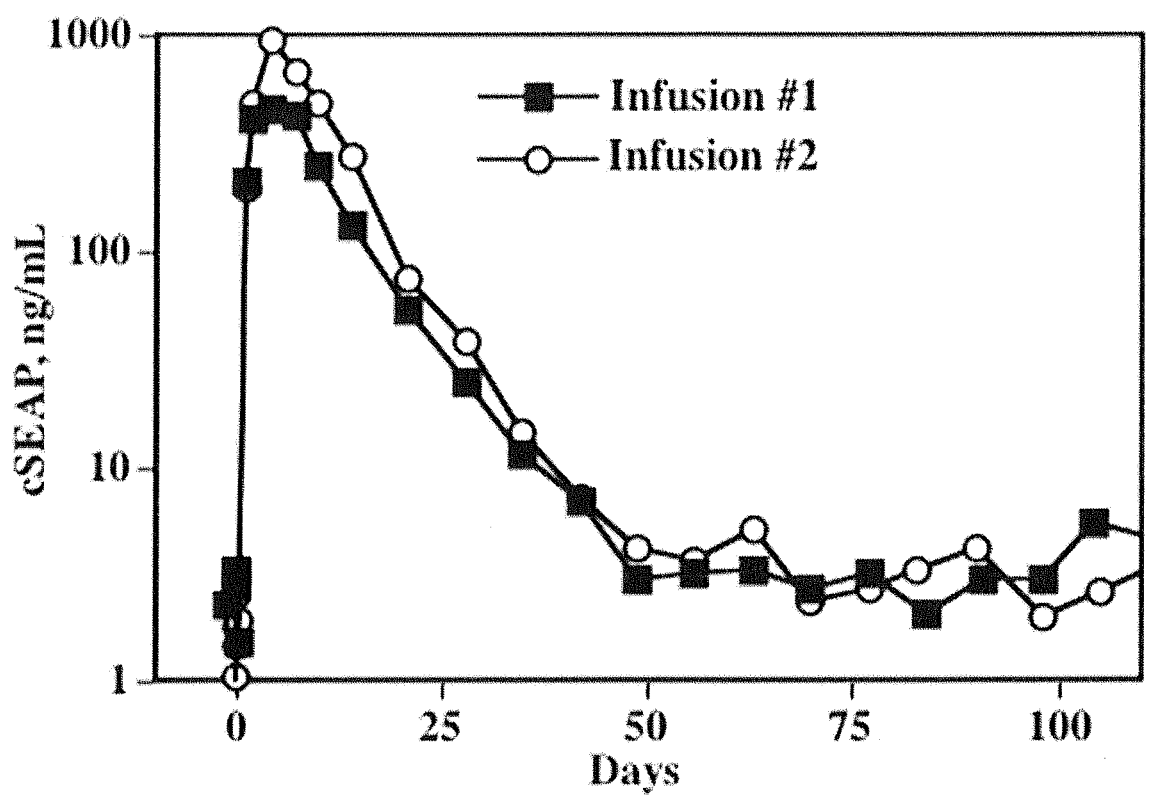
FIG. 6. Canine SEAP expression after hydrodynamic DNA infusion in dogs. Infusions were carried out as described in the text. Plasma samples were collected before, during and after the infusions and assayed for heat-stable alkaline phosphatase activity using a chemiluminescent assay as described in Materials and Methods. Dog #9 was hydrodynamically infused twice, the first time with pKT2/CAGS-cSEAP+pCMVSB100x using the double-balloon strategy (FIG. 1 Panel b) and the second time with pZT2/Clp-cSEAP+pCMVSB100x using the single-balloon strategy into the left hepatic vein (FIG. 1 Panel c). SEAP levels are shown superimposed for both infusions to emphasize the similarity of the expression profiles. SEAP levels observed after day 42 were not significantly different from background pre-infusion levels.

Canine secreted alkaline phosphatase (cSEAP) gene was cloned using a combination of cDNA and synthetic sequences derived from the dog genome database (Olson et al., in preparation) to obtain an alternative reporter gene suitable for evaluation of transgene expression by periodic blood sampling. A CAGS-regulated cSEAP transposon was assembled (pKT2/CAGS-SEAP, FIG. 2) and first tested in mice where it supported a 1000-fold higher than background level of SEAP activity in the plasma one day after hydrodynamic injection. Dog #9 (5.5 kg) was infused with 200 mL containing 2 mg/kg pKT2/CAGS-cSEAP+0.4 mg/kg pCMV-SB100x (FIG. 2) in 10 s using the double-balloon catheter system (FIG. 1b). The dose of transposase gene was reduced due to the increased activity reported for SB100x compared to SB11. Intra-IVC pressure peaked at 128 mm Hg during the infusion (FIG. 5c). Heat-stable cSEAP activity in the peripheral blood peaked on day 4 post-infusion and was clearly detectable out to 42 days post-infusion (FIG. 6). The half-life of transgenic cSEAP was approximately 4.5 days compared to about 1 day for cEPO. Liver enzymes were elevated as in previous infusions and normalized at 2 days to 14 days post-infusion. These results showed that SEAP is an effective and useful model for expression of DNAs.

A second infusion was carried out in Dog #9, which had grown over the intervening five months from 5.5 kg to 9.2 kg. The transposon pZT2/clp-cSEAP (FIG. 2) contained the cSEAP gene in a CpG-less plasmid, including the clp transcriptional motif. In order to maintain approximately a 1:1 infusion volume to target tissue ratio, a single-balloon catheter was used to occlude the major left hepatic vein (LHV) for DNA infusion limited to the left side of the liver (FIG. 1c). 200 ml containing 19 mg of pZT2/clp-cSEAP and 4.4 mg of pCMV-SB100x in Ringer's solution was infused into the LHV through infusion ports distal to the balloon. Intrahepatic venous pressure peaked at 140 mm Hg (FIG. 5d). The animal's liver was evaluated by ultrasound immediately after infusion, and by CT scan two days after infusion; neither test indicated any injury to the liver. After the infusion, heat-stable cSEAP activity in the peripheral blood was observed that, like the earlier infusion, peaked on Day-4 post-infusion and was clearly detectable out to 42 days post-infusion (FIG. 6). As before, liver enzymes were elevated in the circulation immediately after infusion, but normalized two days (AST) to 14 days (ALT) post-infusion. The results from this experiment thus confirmed the value of cSEAP as a reporter and demonstrated effectiveness of delivery to the left side of the liver through the left hepatic vein. However, use of the CpG-less promoter did not prevent the ultimate extinction of cSEAP reporter gene expression, the time course of which was nearly identical to that observed after infusion of pKT2/CAGS-cSEAP.

Kupffer Cell Suppression Results in Extended Expression of Canine Secreted Alkaline Phosphatase.

Figure 7:
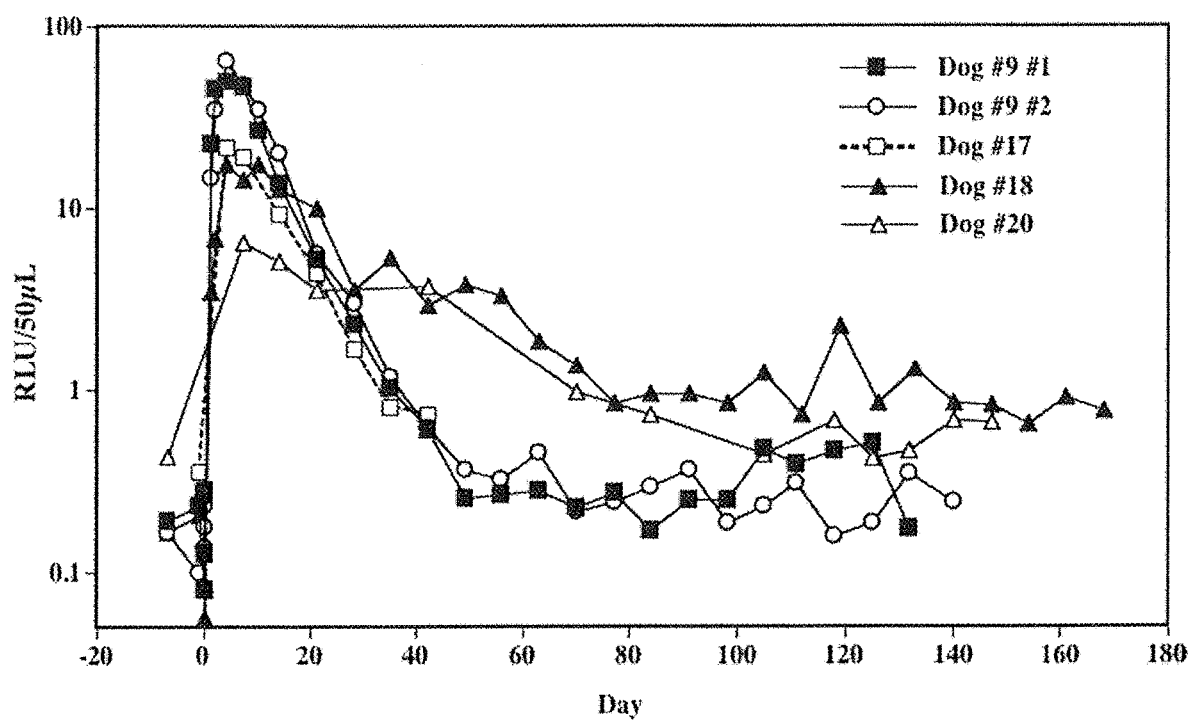
FIG. 7. Effect of cyclophosphamide, dexamethasone, and gadolinium chloride on the time course of canine SEAP expression after hydrodynamic DNA infusion in dogs. Infusions of pKT2/clp-cSEAP//PGK-SB100x (FIG. 2) into the left hepatic vein were carried out as described in the text, collecting plasma samples before, during and after the infusion procedure and assaying for heat stable alkaline phosphatase activity. Dogs #17 and #18 were also administered 1 mg/kg dexamethasone on days −1, 0, 2, 4 (Dog #17) and then twice weekly thereafter for 8 weeks (Dog #18), plus 10 mg/kg cyclophosphamide on day 0 and then weekly thereafter for 6 weeks (Dog #17) or for 3 weeks (Dog #18). Dogs #18 and #20 were also treated with gadolinium chloride on days −1, 0, 2, 4 and then twice weekly thereafter for 12 weeks (Dog #18) or for 5 weeks (Dog #20). Time courses of plasma cSEAP levels for Dog #9 infusions #1 and #2 are plotted for comparison.

A series of experiments were conducted in which pKT2/CLP-cSEAP//PGK-SB100x (encoding both a PGK regulated SB100x sequence as well as the cSEAP encoding transposon) was infused through the left hepatic vein into the left side of the liver (similar to FIG. 1c except the catheter was introduced through the jugular vein, similar to FIG. 1a) to test the effect of several agents on long-term expression; (i) Cyclophosphamide (CP) as an immunosuppressant; (ii) Dexamethasone (Dex), as an anti-inflammatory agent; and (iii) Gadolinium Chloride ($GdCl_3$), to suppress Kupffer cells, the resident macrophage population in the liver. Dog #17 was treated with Dexamethasone 1 mg/kg on days −1, 0, 2, 4 and then twice weekly relative to the time of cSEAP transposon+SB100x transposase DNA infusion. Cyclophosphamide 10 mg/kg was administered on the day of DNA infusion and then weekly thereafter. As seen in FIG. 7, after the initial burst of expression post-infusion, cSEAP expression was extinguished in this animal after about 4 weeks, similar to the time course of expression previously seen (Dog #9, also plotted for comparison). Dog #18 was treated with dexamethasone and cyclophosphamide on the same schedule as Dog #17 relative to balloon catheter-mediated infusion of pKT2/CLP-cSEAP//PGK-SB100x into the LHV, and was additionally treated with gadolinium chloride 10 mg/kg on days −1, 0, 2, 4, and then twice weekly thereafter. In contrast to Dog 17 and Dog 9 and all previous dogs, Dog #18 exhibited extended expression of cSEAP that continued out to 5 months after infusion of pKT2/CLP-cSEAP//PGK-SB100x. Dog #20 was treated with $GdCl_3$ according to the same schedule as Dog #18 relative to balloon catheter mediated infusion of pKT2/CLP-cSEAP//PGK-SB100x, but omitting administration of cyclophosphamide and dexamethasone. Similar to Dog #18, in Dog #20 there was extended expression of cSEAP that continued out to three months post-infusion. Liver samples collected from Dogs #9, #18 and #20 contained 0.001 to 0.01 copies of the cSEAP sequence per genome equivalent of DNA extracted from the left lateral lobe.

Accordingly, the extended cSEAP expression in Dog #18 was most likely a result of administration of a gadolinium compound (GdCl₃) rather than administration of cyclophosphamide and/or dexamethasone because (i) administration of dexamethasone and cyclophosphamide in the absence of the gadolinium compound did not result in extended expression of cSEAP in Dog #17 (FIG. 7), and (ii) extended expression of cSEAP was observed in Dog #20, which was administered GdCl₃ but was not administered dexamethasone nor cyclophosphamide. These studies showed that administration of a gadolinium compound in association with an introduction of DNA into the liver brings about an extension in the period of gene expression. These results were achieved in the dog, a large animal model highly relevant for human clinical treatments.

Kupffer Cell Inhibition, Delivery, and Administration

Kupffer cells can be suppressed in various ways. The term suppressed, in this context, is broad, and includes depleting populations of the cells, stunning Kupffer cell metabolic activity, and blocking or otherwise inactivating Kupffer cell functions. Certain gadolinium chlorides suppress Kupffer cells. Other substances that have been reported for inhibition of Kupffer cells are, for instance: silibinin, dichloromethylene diphosphonate, gadolinium chloride, and clodronate. The actions of silibinin are described in, e.g., "Inhibition of Kupffer Cell Functions as an Explanation for the Hepatoprotective Properties of Silibinin", DEHMLOW et al., HEPATOLOGY 1996; 23:749-754.

Gadolinium trichloride is not to be confused with the imaging agent referred to as gadolinium contrast agent. The contrast agent is chelated with gadolinium at three or more points. In contrast, gadolinium trichloride is not chelated. The chelation of gadolinium for imaging purposes is performed to make the contrast agent non-toxic; the contrast agent does not suppress Kupffer cells. The ionic form of gadolinium has the Kupffer-cell inhibitory effect. Thus an embodiment of a Kupffer cell-suppressing substance, upon dissolution in aqueous solution, comprises a free gadolinium (III) ion, i.e., the substance is comprised of gadolinium in a form that is soluble in aqueous media such that it substantially dissolves and makes the gadolinium(III) ion available. Substances that are insoluble in water, or release gadolinium ions in insubstantial amounts might, in theory, have some small solubility but do not substantially dissolve to release the ion. Thus a chelated gadolinium contrast agent that theoretically released some small amount of gadolinium(III) ions is excluded. Aqueous media is a broad term that includes water, saline solution, and blood. The Kupffer cell-suppressing substance may be free of chelating agents that form three or more coordinate bonds with the gadolinium atom. Or the Kupffer cell-suppressing substance may be free of all chelating agents. The substance comprising the Gadolinium may be a gadolinium(III) salt, e.g., a salt with a halide, and may be Gd(Cl)₃.

There are a variety of options for delivering these substances. Any suitable biomedical vehicle may be used. The action of the Kupffer cell-suppressing substance is in the liver, which rapidly receives substances from the blood. Accordingly, delivery vehicles include direct percutaneous injection into the vasculature or the liver, liposomes, microspheres, micelles, particles, microparticles, nanoparticles, fusion molecules comprising a targeting moiety, and coatings on a device disposed at or near the liver.

The timing of administration of the inhibitory substance can be before, during, or after administration of an exogenous nucleic acid, e.g., a transposon or another vector comprising the exogenous nucleic acid. The inhibitory substance may be readministered from time to time after the treatment begins. Twice weekly administration has been useful. Other options include, e.g, at least once a week for a number of weeks from 2-52 weeks; artisans will immediately appreciate that all values and ranges between the explicitly stated values are contemplated and are incorporated herein as if written in detail.

Introduction of DNA to the Patient, Vectors, and Nucleic Acids

Kupffer cell suppression is a method of extending exogenous DNA expression regardless of the particular DNA expression method that is used, or the DNA that is expressed. A variety of nucleic acids may be introduced into the animal or cells. As used herein, the term nucleic acid includes DNA, RNA, and nucleic acid analogs, and nucleic acids that are double-stranded or single-stranded (i.e., a sense or an antisense single strand). Nucleic acid analogs can be modified at the base moiety, sugar moiety, or phosphate backbone to improve, for example, stability, hybridization, or solubility of the nucleic acid. The exogenous nucleic acid (also referred to herein as a target nucleic acid sequence) can be operably linked to a regulatory region such as a promoter. As used herein, operably linked refers to positioning of a regulatory region relative to a nucleic acid sequence in such a way as to permit or facilitate transcription of the target nucleic acid.

Any type of promoter can be operably linked to a target nucleic acid sequence. Examples of promoters include, without limitation, tissue-specific promoters, constitutive promoters, and promoters responsive or unresponsive to a particular stimulus. Suitable tissue specific promoters can result in preferential expression of a nucleic acid transcript in beta cells and include, for example, the human insulin promoter. Other tissue specific promoters can result in preferential expression in, for example, hepatocytes and can include the albumin or other promoters. In other embodiments, a promoter that facilitates the expression of a nucleic acid molecule without significant tissue- or temporal-specificity can be used (i.e., a constitutive promoter). For example, a beta-actin promoter such as a beta-actin gene promoter, ubiquitin promoter, miniCAGs promoter, glyceraldehyde-3-phosphate dehydrogenase (GAPDH) promoter, or 3-phosphoglycerate kinase (PGK) promoter can be used, as well as viral promoters such as the herpes simplex virus thymidine kinase (HSV-TK) promoter, the SV40 promoter, or a cytomegalovirus (CMV) promoter. In some embodiments, a fusion of the chicken beta actin gene promoter and the CMV enhancer is used as a promoter. See, for example, Xu et al. (2001) Hum. Gene Ther. 12:563; and Kiwaki et al. (1996) Hum. Gene Ther. 7:821.

An example of an inducible promoter is the Tet-Off system wherein administration of tetracycline turns off expression. Another system is the tetracycline (tet)-on promoter system, which can be used to regulate transcription of the nucleic acid. In this system, a mutated Tet repressor (TetR) is fused to the activation domain of herpes simplex virus VP16 trans-activator protein to create a recombinant tetracycline-controlled transcriptional activator (rtTA), which is regulated by tet or doxycycline (dox). In the absence of antibiotic, transcription is minimal, while in the presence of tet or dox, transcription is induced. Alternative inducible systems include the ecdysone or rapamycin systems. Ecdysone is an insect molting hormone whose production is controlled by a heterodimer of the ecdysone receptor and the product of the ultraspiracle gene (USP). Expression is induced by treatment with ecdysone or an analog of ecdysone such as muristerone A. The agent that is administered to the animal to trigger the inducible system is referred to as an induction agent.

Additional regulatory regions that may be useful in nucleic acid constructs, include, but are not limited to, polyadenylation sequences, translation control sequences (e.g., an internal ribosome entry segment, IRES), enhancers, inducible elements, or introns. Such regulatory regions may not be necessary, although they may increase expression by affecting transcription, stability of the mRNA, translational efficiency, or the like. Such regulatory regions can be included in a nucleic acid construct as desired to obtain optimal expression of the nucleic acids in the cell(s). Sufficient expression, however, can sometimes be obtained without such additional elements.

A nucleic acid construct may be used that encodes signal peptides or selectable markers. Signal peptides can be used such that an encoded polypeptide is directed to a particular cellular location (e.g., the cell surface). Non-limiting examples of selectable markers include puromycin, ganciclovir, adenosine deaminase (ADA), aminoglycoside phosphotransferase (neo, G418, APH), dihydrofolate reductase (DHFR), hygromycin-B-phosphtransferase, thymidine kinase (TK), and xanthine-guanine phosphoribosyltransferase (XGPRT). Such markers are useful for selecting stable transformants in culture. Other selectable markers include fluorescent polypeptides, such as green fluorescent protein or yellow fluorescent protein.

In some embodiments, the target nucleic acid encodes a polypeptide. A nucleic acid sequence encoding a polypeptide can include a tag sequence that encodes a "tag" designed to facilitate subsequent manipulation of the encoded polypeptide (e.g., to facilitate localization or detection). Tag sequences can be inserted in the nucleic acid sequence encoding the polypeptide such that the encoded tag is located at either the carboxyl or amino terminus of the polypeptide. Non-limiting examples of encoded tags include glutathione S-transferase (GST) and FLAG™ tag (Kodak, New Haven, Conn.). Treatment of humans includes embodiments that are free of tags (and free of markers and free of signals).

In transposon systems, the transcriptional unit of a nucleic acid construct, i.e., the regulatory region operably linked to a target nucleic acid sequence, is flanked by an inverted repeat of a transposon. Several transposon systems, including, for example, Sleeping Beauty (see, U.S. Pat. No. 6,613,752 and U.S. Publication No. 2005/0003542); Frog Prince (Miskey et al. (2003) Nucleic Acids Res. 31:6873); Tol2 (Kawakami (2007) Genome Biology 8(Suppl. 1):S7; Minos (Pavlopoulos et al. (2007) Genome Biology 8(Suppl. 1):S2); Hsmar1 (Miskey et al. (2007)) Mol Cell Biol. 27:4589); and Passport have been developed to introduce nucleic acids into cells, including mice, human, and pig cells. The Sleeping Beauty system is particularly useful—including the original Sleeping Beauty and its various improved transposases and/or transposons. A transposase can be delivered as a protein, encoded on the same nucleic acid construct as the target nucleic acid, can be introduced on a separate nucleic acid construct, or provided as an mRNA (e.g., an in vitro-transcribed and capped mRNA).

Insulator elements also can be included in a nucleic acid construct to maintain expression of the target nucleic acid and to inhibit the unwanted transcription of host genes. See, for example, U.S. Publication No. 2004/0203158. Typically, an insulator element flanks each side of the transcriptional unit and is internal to the inverted repeat of the transposon. Non-limiting examples of insulator elements include the matrix attachment region-(MAR) type insulator elements and border-type insulator elements. See, for example, U.S. Pat. Nos. 6,395,549, 5,731,178, 6,100,448 and 5,610,053, and U.S. Publication No. 2004/0203158.

Nucleic acids can be incorporated into vectors. A vector is a broad term that includes any specific nucleic acid segment that is designed to move nucleic acid from a carrier into a target. A vector may be referred to as an expression vector, or a vector system, which is a set of components needed to bring about DNA insertion into a genome or other targeted DNA sequence such as an episome, plasmid, or even virus/phage DNA segment. Some vector systems including some viral vectors (e.g., retroviruses and integrating phage viruses), and non-viral vectors (e.g., transposons) used for gene delivery in animals have two basic components: 1) a vector comprised of DNA (or RNA that is reverse transcribed into a cDNA) and 2) a transposase, recombinase, or other integrase enzyme that recognizes both the vector and a DNA target sequence and inserts the vector into the chromosomal DNA. Vectors most often contain one or more expression cassettes that comprise one or more expression control sequences, wherein an expression control sequence is a DNA sequence that controls and regulates the transcription and/or translation of another DNA sequence or mRNA, respectively.

Many different types of vectors are known. For example, plasmids and viral vectors, e.g., retroviral vectors, are known. Mammalian expression plasmids typically have an origin of replication, a suitable promoter and optional enhancer, and also any necessary ribosome binding sites, a polyadenylation site, splice donor and acceptor sites, transcriptional termination sequences, and 5' flanking non-transcribed sequences. Examples of vectors include: plasmids (which may also be a carrier of another type of vector), adenovirus, adeno-associated virus (AAV), lentivirus (e.g., HIV-1, SIV or FIV), retrovirus (e.g., ASV, ALV or MoMLV), and transposons (e.g., Sleeping Beauty, P-elements, Tol-2, Frog Prince, piggyBac).

As used herein, the term nucleic acid refers to both RNA and DNA, including, for example, cDNA, genomic DNA, synthetic (e.g., chemically synthesized) DNA, as well as naturally occurring and chemically modified nucleic acids, e.g., synthetic bases or alternative backbones. A nucleic acid molecule can be double-stranded or single-stranded (e.g., a sense or an antisense single strand).

Nucleic Acid Delivery with Non-Viral Vectors

DNA and nucleic acids can be delivered non-virally. Options include, e.g. cations, lipids, naked DNA, artificial chromosomes, plasmids, conjugate, polycation conjugates, cationic polymers, polymeric and molecular conjugates, and other physical methods of DNA delivery such as electroporation, ultrasound, and biolistic delivery.

Some systems are cationic. They interact with negatively charged DNA through electrostatic interactions and provide an overall positive net charge that helps the materials interact with negatively charged cell membranes and be internalized into the cell. The most widely studied polymers for gene therapy include poly L-lysine (PLL) and polyethylenimine (PEI). Several polycations possessing sustainable buffering capacity below physiological pH, such as lipopolyamines and polyamidoamine polymers are efficient transfection agents. One or more of such agents can be combined with the nucleic acid and other materials. For instance, liver targeting can be enhanced by an addition of asialoglycoprotein receptors using a complex of poly-L-lysine (PLL) condensed DNA and galactosylated bovine serum albumin (GalBSA) via charge interaction (Han et al., 1999). Asialoglycoprotein and the like can be used with other vehicles. Uddin and Islam (attached) provide an overview of various systems.

Targeted nucleases are also useful for introducing DNA into cells. Targeted nucleases include zinc fingers, TALENs, and Cas9/CRISPR systems. In general, a target DNA site is identified and a targeted nuclease is created that will specifically bind to the site. The targeted nuclease is delivered to the cell or embryo, e.g., as a protein, mRNA or by a vector that encodes the nuclease. The targeted nuclease cleaves the DNA to make a break that is then repaired, often resulting in the creation of an indel, or incorporating sequences or polymorphisms contained in an accompanying exogenous nucleic acid that is either inserted or serves as a template for repair of the break with a modified sequence. The term exogenous nucleic acid means a nucleic acid that is added to the cell or embryo, regardless of whether the nucleic acid is the same or distinct from nucleic acid sequences naturally in the cell. An exogenous sequence refers to a sequence used to change the target cell, regardless of whether the sequence is actually a nucleic acid inserted into chromosomal DNA or if the sequence is used as a template to change the cellular DNA. Moreover, chromosomal DNA may be altered with an exogenous nucleic acid that does not actually encode a therapeutic agent; instead, the nucleic acid is a template for repair caused by a targeted nuclease. The repair allows the expression of the therapeutic agent. It can be useful to nonetheless suppress Kupffer cell activity for the sake of allowing effective repairs and also to accommodate expression of factors that the cell, and patient, has not yet expressed, e.g., a new blood factor.

In this context, it can be seen that an exogenous DNA can express an exogenous therapeutic agent or an endogenous therapeutic agent. Endogenous, in this context, means the patient's repaired protein or other factor. The therapeutic agent may be biological, meaning it is a factor that is naturally found in the biological system of the patient, e.g., a human blood factor in a human. The biological factor would normally be expressed from an allele from the same species, although there are circumstances where expressing a factor from another species is called for. A type of therapeutic agent could be an antibody, an antibody fragment, or a scFv. Another type of therapeutic agent is an antigen.

Vehicles

Vectors and/or substances that inhibit Kupffer cells may be incorporated into various vehicles to facilitate their use. Further, DNA delivery can be accomplished through many of these same techniques. Moreover, embodiments include targeting the vehicles specifically to a liver and/or specifically to a liver cell, e.g., hepatocyte or Kupffer cell. Particles, e.g, liposomes, microcapsules, nanoparticles, or microparticles, can be utilized, such as those formed from copolymers of poly(ethylene glycol) and poly(lactic acid), those formed from copolymers of poly(ethylene oxide) and poly(beta-amino ester), and those formed from proteins or polysaccharides. Further materials are, e.g., biodegradable polymers may also be used, e.g., polylactic acid, polyglycolic acid, copolymers of polylactic and polyglycolic acid, polycaprolactones, polyhydroxy butyric acid, polyorthoesters, polyacetals, polydihydropyrans, and polycyanoacylates. Polyethyleeneimine and polylysine are also useful for delivery of substances. Other particle vehicle systems are known to artisans. See also Devalapally et al., Cancer Chemother Pharmacol., 07-25-06; Langer et al., International Journal of Pharmaceutics, 257:169-180 (2003); and Tobio et al., Pharmaceutical Research, 15(2):270-275 (1998). And, for instance, certain techniques for making microparticles are set forth in U.S. Pat. Nos. 5,227,165, 6,022,564, 6,090,925, and 6,224,794.

Functionalization of particles to employ targeting capability requires association of a targeting polypeptide or other targeting moiety, e.g., lectin or polysaccharide, with the particle, e.g., by covalent binding using a bioconjugation technique, with choice of a particular technique being guided by the particle or nanoparticle, or other construct to which the polypeptide is to be joined. In general, many bioconjugation techniques for attaching targeting moieties to other materials are well known and the most suitable technique may be chosen for a particular material.

Conjugation may be accomplished by covalent bonding of the peptide to another molecule, with or without use of a linker. The formation of such conjugates is within the skill of artisans and various techniques are known for accomplishing the conjugation, with the choice of the particular technique being guided by the materials to be conjugated. The addition of amino acids to the polypeptide (C- or N-terminal) which contain ionizable side chains, i.e. aspartic acid, glutamic acid, lysine, arginine, cysteine, histidine, or tyrosine, and are not contained in the active portion of the polypeptide sequence, serve in their unprotonated state as a potent nucleophile to engage in various bioconjugation reactions with reactive groups attached to polymers, i.e. homo- or hetero-bi-functional PEG (e.g., Lutolf and Hubbell, Biomacromolecules 2003; 4:713-22, Hermanson, Bioconjugate Techniques, London. Academic Press Ltd; 1996). In some embodiments, a soluble polymer linker is used, and may be administered to a patient in a pharmaceutically acceptable form. Or a drug may be encapsulated in polymerosomes or vesicles or covalently attached to the peptide ligand.

Administration

Pharmaceutically acceptable carriers or excipients may be used to deliver embodiments, e.g., Kupffer cell-suppressing substances, as described herein. Excipient refers to an inert substance used as a diluent or vehicle for a therapeutic agent. Pharmaceutically acceptable carriers are used, in general, with a compound so as to make the compound useful for a therapy or as a product. In general, for any substance, a pharmaceutically acceptable carrier is a material that is combined with the substance for delivery to an animal. In some cases the carrier is essential for delivery, e.g., to solubilize an insoluble compound for liquid delivery; a buffer for control of the pH of the substance to preserve its activity; or a diluent to prevent loss of the substance in the storage vessel. In other cases, however, the carrier is for convenience, e.g., a liquid for more convenient administration. Pharmaceutically acceptable salts of the compounds described herein may be synthesized according to methods known to those skilled in the arts. Thus pharmaceutically acceptable compositions are highly purified to be free of contaminants, are sterile, biocompatible and not toxic beyond their intended level of toxicity or targeted-toxicity, and further may include a carrier, salt, or excipient suited to administration to a patient. In the case of water as the carrier, the water is highly purified and processed to be free of contaminants, e.g., endotoxins.

The compounds described herein may be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. Thus the deliverable compound may be made in a form suitable for oral, rectal, topical, intravenous injection, intra-articular injection, or parenteral administration. Carriers include solids or liquids, and the type of carrier is chosen based on the type of administration being used. Suitable binders, lubricants, disintegrating agents, coloring agents, flavoring agents, flow-inducing agents, and melting agents may be included as carriers, e.g., for pills. For instance, an active component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. The compounds can be administered orally in solid dosage forms, such as capsules, tablets, and powders, or in liquid dosage forms, such as elixirs, syrups, and suspensions. The active compounds can also be administered parentally, in sterile liquid dosage forms. Buffers for achieving a physiological pH or osmolarity may also be used.

Long-Term Therapeutic Agent Expression

The invention is not limited to a particular therapeutic agent. Some embodiments of the invention are, however, directed to certain agents. One such agent is EPO. This factor was successfully expressed in the animal models. Similarly, other such agents are clotting Factor VIII, clotting Factor IX, and blood factors. Other such agents are a protein, an antibody, an antibody fragment, an scFv, and an antigen.

Factor VIII and Factor IX are blood factors that are absent in certain disease states. Blood factor is a term referring to a protein found in blood that mediates a coagulation or response of the blood, referring to the contact activation pathway (also known as the intrinsic pathway), the tissue factor pathway, and the common pathway. Such proteins include factor VII, factor VIII, factor IX, fibrinogen, thrombin, factor X, factor XII, high-molecular-weight kininogen (HMWK), prekallikrein, protein C, and thrombomodulin.

Additional Materials and Methods

Catheters and Placement.

National and local standards for testing and animal care were followed. With the animal under general anesthesia and using sterile technique, a cut down to the femoral vein or the lateral jugular vein is performed, and an appropriately sized introducer sheath (such as an 11 Fr Pinnacle 16035-11) is placed into the vessel using Seldinger technique. Various strategies can used for balloon-mediated occlusion of the liver with subsequent infusion of DNA into the hepatic venous circulation (FIG. 1).

Figure 1:
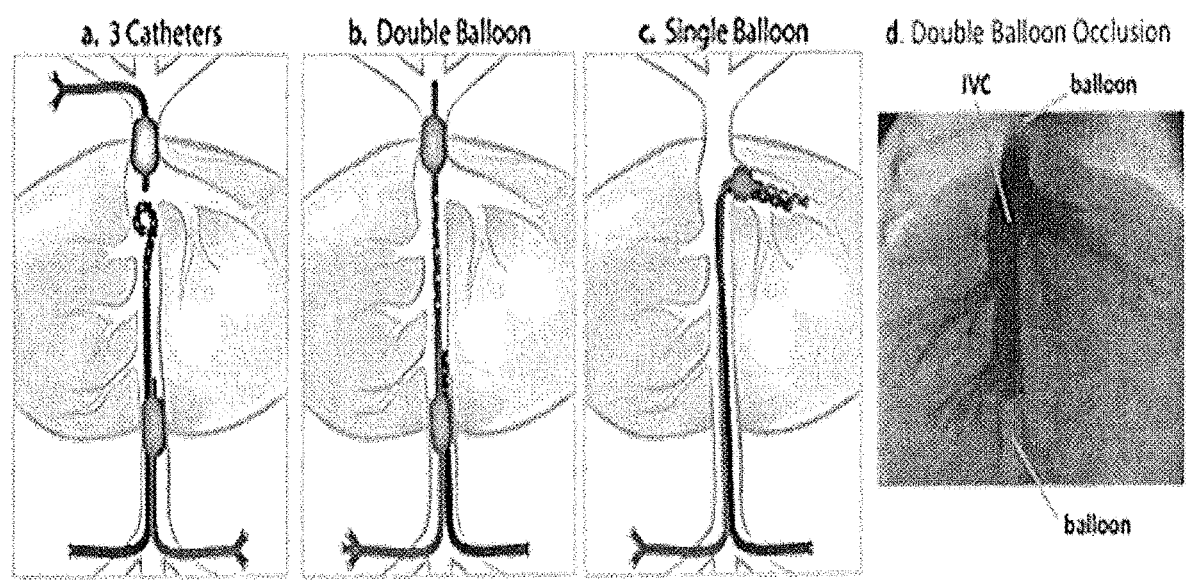
FIG. 1. Strategies for catheter-mediated DNA delivery to dog liver. Single and double balloon-catheters are introduced through the femoral vein as indicated. A single-balloon catheter is introduced through the jugular vein as indicated. Additional catheters introduced for infusion of DNA (a) or to monitor intravascular pressure (b and c) are shown. Panel (a) Three-catheter strategy used for infusion into the whole liver in Dog #6. Panel (b) Double-balloon strategy for occlusion of the inferior vena cava (IVC) and infusion of DNA through the same catheter in Dogs #7, #8 (infusions #1 and #2) and #9 (infusion #1). Panel (c) Single-balloon strategy used for infusion into the left hepatic vein in Dog #9 (infusion #2). Panel (d) Venogram image of Dog #8 (infusion #2) prior to hydrodynamic delivery. The balloons have been inflated and contrast dye slowly infused into the IVC to show correct positioning of the catheter, complete occlusion of the IVC, and extensive vascular access to the liver through the hepatic veins.

Referring to FIG. 1: Three catheter system (FIG. 1a): (i) A 6 Fr single-balloon wedge pressure or Berman angiographic balloon catheter (such as Arrow #AI-07126 or AI-07131) is introduced through the right femoral vein to the IVC immediately below the liver; (ii) A second 6 Fr single-balloon catheter is introduced through the jugular vein to the IVC immediately above the liver. (iii) A high-flow pigtail catheter (such as 8 Fr Cordis #801-618 or 4 Fr Vanguard Dx Medrad pigtail #155, 1200 PSI) is introduced through the left femoral vein past the lower balloon-catheter into the region of the hepatic veins in the IVC. 2. Double balloon system (FIG. 1b): A custom-designed catheter (5 Fr or similar in size) is assembled to contain the following components: (i) Two balloons positioned such that upon inflation there is occlusion of the liver and the entire IVC; (ii) A separate lumen for inflation of the balloons; (iii) a second lumen with multiple outlet ports in the surface of the catheter positioned between the two balloons for infusion of the DNA. The catheter is introduced through the right femoral vein into the IVC and a second pressure-sensing catheter is introduced through the left femoral vein with the end of the catheter positioned between the two balloons. 3. Single balloon system (FIG. 1c): A custom-designed catheter (8 Fr or similar in size) is assembled to contain a single compliant balloon and multiple ports positioned distal to the balloon for delivery of DNA solution. This catheter is introduced through the right femoral vein or the jugular vein into the IVC and positioned just inside the left hepatic vein (LHV). A second pressure-sensing catheter is introduced alongside the balloon catheter with the end of the catheter positioned distal to the balloon.

DNA Infusions.

Fluoroscopy is used to position the catheters, and then the balloons are briefly inflated and a small amount of contrast agent is infused by hand to verify correct catheter placement, occlusion of the IVC and access to the hepatic venous circulation (FIG. 1d). The balloons are then deflated and a DNA-containing solution (for instance, transposon and transposase-encoding DNA in Ringer's solution) is loaded into a MEDRAD angiographic injector head system. The balloons are re-inflated, and then the desired amount of DNA solution is infused over the desired amount of time (usually within 17 seconds). Intrahepatic pressures are collected before, during and after infusion of DNA solution. After the infusion, the animals cut-down is surgically repaired. Venous blood samples are collected before, during and after the procedure for analysis of clinical response and to measure transgene expression. At the end of each experiment, animals are given heparin at 150 units/kg i.v. and then anesthetized with propofol at 2-6 mg/kg i.v. After sacrifice, a gross general necropsy is performed and samples of liver tissue are collected for molecular genetic analyses.

Transgene Expression Assays.

Plasma samples from either pKT2/CAGS-cEPO//Ub-SB11- or pKT2/CLP-cEPO//CMV-SB100x-infused animals (FIG. 2) were assayed by ELISA for canine EPO using the Quantikine IVD Human Erythropoietin kit from R & D Systems (Minneapolis, Minn.). Canine EPO amounts are reported in miU/ml. Plasma samples from pKT2/CAGS-cSEAP, pZT2/CLP-cSEAP or pKT2/CLP-cSEAP//PGK-SB100x infused animals were heated for 10 min. at 65° C. and then assayed for SEAP using TROPIX PHOSPHA phospholuminescent substrate (Applied Biosytems) with human SEAP as a positive control and reporting results in RLU/50 microliters.

TABLE 1

Summary of Hydrodynamic DNA Infusions into Dogs

| No. | Wt. (kg) | DNA (mg) | Rate (vol/time) | Route[a] | Peak ALT (U/L) | Maximum Expression |
|---|---|---|---|---|---|---|
| 6 | 5.6 | 60[b] | 200 ml/17 s | IVC | 2178 | 150 miU/ml EPO |
| 7 | 5.6 | 60[b] | 200 ml/10 s | IVC | 2146 | 2010 miU/ml EPO |
| 8 | 6.8 | 60[c] | 200 ml/10 s | IVC | 3177 | 2100 miU/ml EPO |
| 8#2 | 9.8 | 18[c] | 200 ml/10 s | IVC | 1343 | 980 miU/ml EPO |
| 9 | 5.5 | 11[d] | 200 ml/10 s | IVC | 6102 | 49 RLU/50 μL SEAP |
| 9#2 | 9.1 | 12.6[e] | 202 ml/18 s | LHV | 6827 | 64 RLU/50 μL SEAP |

TABLE 1-continued

Summary of Hydrodynamic DNA Infusions into Dogs

| No. | Wt. (kg) | DNA (mg) | Rate (vol/time) | Route[a] | Peak ALT (U/L) | Maximum Expression |
|---|---|---|---|---|---|---|
| 17 | 5.8 | 11.6[f] | 199 ml/18 s | LHV | 5986 | 21 RLU/50 μL SEAP |
| 18 | 6.2 | 12.4[f] | 195 ml/8 s | LHV | 447 | 35 RLU/50 μL SEAP |
| 20 | 5.1 | 10.2[f] | 200 ml/8 s | LHV | 778 | 6.5 RLU/50 μL SEAP |

[a]Route: venous infusion to the whole liver (IVC); venous infusion into the left half of the liver through the left hepatic vein (LHV)
[b]pKT2/CAGS-cEPO//Ub-SB11
[c]pKT2/clp-cEPO//CMV-SB100x
[d]pKT2/CAGS-cSEAP + 2.2 mg pCMV-SB100x
[e]pKT2/clp-cSEAP + 2.0 mg pCMV-SB100x
[f]pKT2/clp-cSEAP//PGK-SB100x Patents, patent applications, publications, and references set forth herein are hereby incorporated herein by reference for all purposes. In case of conflict, the instant specification is controlling. Headings are provided for convenience of the reader and are non-limiting with respect to substantive matters.

The invention claimed is:

1. A method of treating a human patient to express a therapeutic agent, comprising administering a Kupffer cell-suppressing substance in combination with a vehicle for introducing, into the human patient, an exogenous nucleic acid comprising a sequence for expression of the agent, wherein the Kupffer cell-suppressing substance, upon dissolution in aqueous solution, comprises a free gadolinium (III) ion,
    wherein the method comprises administering the Kupffer cell-suppressing substance within 24 hours prior to administering the exogenous nucleic acid and also at a time between 1 and 10 days after administering the exogenous nucleic acid.

2. The method of claim 1 wherein the Kupffer cell-suppressing substance comprises a gadolinium(III) salt.

3. The method of claim 2 wherein the salt comprises a halide.

4. The method of claim 3 wherein the salt comprises Gd(Cl)3.

5. The method of claim 1 wherein the therapeutic agent is chosen from the group consisting of erythropoietin, clotting Factor VIII, clotting Factor IX, an antibody, an antibody fragment, an scFv, and an antigen.

6. The method of claim 1 wherein the vehicle comprises a vector.

7. The method of claim 6 wherein the vector is chosen from the group consisting of an adenovirus, a lentivirus, a retrovirus, an adeno-associated virus, an integrating phage vector, a non-viral vector, a transposon and/or transposase, an integrase substrate, and a plasmid.

8. The method of claim 1 wherein the vehicle comprises a targeted nuclease for integrating the exogenous nucleic acid.

9. The method of claim 1 wherein the vehicle is chosen from the group consisting of liposomes, microspheres, micelles, microparticles, nanoparticles, and coatings on a device disposed at or near the liver.

10. The method of claim 1 wherein the Kupffer cell-suppressing substance is administered before, during, or after administration of the exogenous nucleic acid.

11. The method of claim 1 with the Kupffer cell-suppressing substance being administered by a method chosen from the group consisting of intravenous, intramuscular, subcutaneous, and percutaneous injection, and hydrodynamically to the liver.

12. A method of treating a human patient for expression of a gene comprising administering, to a human, an exogeneous nucleic acid that expresses the gene in combination with a Kupffer cell-suppressing substance that comprises a gadolinium atom that is free of chelating agents that form three or more coordinate bonds with the gadolinium atom,
    wherein the method comprises administering the Kupffer cell-suppressing substance within 24 hours prior to administering the exogenous nucleic acid and also at a time between 1 and 10 days after administering the exogenous nucleic acid.

13. The method of claim 1 wherein the therapeutic agent is a protein.

14. The method of claim 1 wherein the therapeutic agent is a blood factor.

* * * * *